United States Patent
Hassler, Jr. et al.

(10) Patent No.: US 7,599,743 B2
(45) Date of Patent: Oct. 6, 2009

(54) LOW FREQUENCY TRANSCUTANEOUS ENERGY TRANSFER TO IMPLANTED MEDICAL DEVICE

(75) Inventors: William L. Hassler, Jr., Cincinnati, OH (US); Daniel F. Dlugos, Jr., Morrow, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 400 days.

(21) Appl. No.: 10/876,307

(22) Filed: Jun. 24, 2004

(65) Prior Publication Data

US 2005/0288741 A1   Dec. 29, 2005

(51) Int. Cl.
*A61N 1/40* (2006.01)

(52) U.S. Cl. .............................. 607/61; 607/40; 607/65

(58) Field of Classification Search ................... 607/33, 607/34, 40, 61, 65
See application file for complete search history.

(56) References Cited

U.S. PATENT DOCUMENTS

| | | | |
|---|---|---|---|
| 3,727,616 A * | 4/1973 | Lenzkes ....................... 607/59 |
| 3,867,950 A | 2/1975 | Fischell | |
| 4,096,866 A | 6/1978 | Fischell | |
| 4,281,664 A | 8/1981 | Duggan | |
| 4,361,153 A * | 11/1982 | Slocum et al. ................. 607/32 |
| 4,441,210 A * | 4/1984 | Hochmair et al. ........... 455/41.1 |
| 4,581,018 A | 4/1986 | Jassawalla et al. | |
| 4,611,598 A * | 9/1986 | Hortmann et al. ............. 607/57 |
| 4,665,896 A | 5/1987 | LaForge et al. | |
| 4,681,111 A | 7/1987 | Silvian | |
| 5,109,843 A | 5/1992 | Melvin et al. | |
| 5,350,413 A * | 9/1994 | Miller .......................... 607/61 |
| 5,507,737 A | 4/1996 | Palmskog | |
| 5,690,693 A | 11/1997 | Wang et al. | |
| 5,715,837 A * | 2/1998 | Chen .......................... 128/899 |
| 5,733,313 A | 3/1998 | Barreras, Sr. et al. | |
| 5,741,315 A | 4/1998 | Lee et al. | |
| 5,741,316 A | 4/1998 | Chen et al. | |
| 5,938,669 A | 8/1999 | Klaiber et al. | |
| 5,974,873 A | 11/1999 | Nelson | |
| 5,991,664 A | 11/1999 | Seligman | |
| 6,058,330 A | 5/2000 | Borza | |

(Continued)

FOREIGN PATENT DOCUMENTS

GB   2 239 802   7/1991

(Continued)

OTHER PUBLICATIONS

USPTO Office Action for U.S. Appl. No. 10/876,058, dated May 23, 2006.

(Continued)

*Primary Examiner*—Carl H Layno
*Assistant Examiner*—Eugene T Wu
(74) *Attorney, Agent, or Firm*—Frost Brown Todd LLC (57) ABSTRACT

An implantable medical device system advantageously utilizes low frequency (e.g., about 1-100 kHz) transcutaneous energy transfer (TET) for supplying power from an external control module to an implantable medical device, avoiding power dissipation through eddy currents in a metallic case of an implant and/or in human tissue, thereby enabling smaller implants using a metallic case such as titanium and/or allowing TET signals of greater strength thereby allowing placement more deeply within a patient without excessive power transfer inefficiencies.

6 Claims, 6 Drawing Sheets

U.S. PATENT DOCUMENTS

| | | |
|---|---|---|
| 6,102,678 A | 8/2000 | Peclat |
| 6,115,636 A | 9/2000 | Ryan |
| 6,208,894 B1 | 3/2001 | Schulman et al. |
| 6,315,769 B1 | 11/2001 | Peer et al. |
| 6,324,431 B1 | 11/2001 | Zarinetchi et al. |
| 6,327,504 B1 | 12/2001 | Dolgin et al. |
| 6,366,817 B1 | 4/2002 | Kung |
| 6,430,444 B1 | 8/2002 | Borza |
| 6,463,329 B1 | 10/2002 | Goedeke |
| 6,482,177 B1 | 11/2002 | Leinders |
| 6,505,077 B1 * | 1/2003 | Kast et al. ............ 607/61 |
| 6,542,350 B1 | 4/2003 | Rogers |
| 6,585,763 B1 | 7/2003 | Keilman et al. |
| 6,889,087 B2 | 5/2005 | Moore |
| 6,895,281 B1 | 5/2005 | Amundson et al. |
| 7,016,733 B2 | 3/2006 | Dublin et al. |
| 7,092,762 B1 | 8/2006 | Loftin et al. |
| 7,191,007 B2 | 3/2007 | Desai et al. |
| 7,225,032 B2 | 5/2007 | Schmeling et al. |
| 7,286,881 B2 | 10/2007 | Schommer et al. |
| 2002/0055763 A1 | 5/2002 | Zarinetchi et al. |
| 2002/0087204 A1 | 7/2002 | Kung et al. |
| 2002/0177884 A1 * | 11/2002 | Ahn et al. ............ 607/61 |
| 2004/0095333 A1 * | 5/2004 | Morag et al. ......... 345/173 |
| 2004/0138725 A1 | 7/2004 | Forsell |
| 2005/0075694 A1 * | 4/2005 | Schmeling et al. ..... 607/61 |
| 2005/0228740 A1 | 10/2005 | Chang et al. |
| 2005/0228742 A1 | 10/2005 | McHale et al. |
| 2005/0288739 A1 | 12/2005 | Hassler, Jr. et al. |
| 2005/0288740 A1 | 12/2005 | Hassler et al. |
| 2005/0288742 A1 | 12/2005 | Giordano et al. |
| 2006/0155347 A1 * | 7/2006 | Forsell ............ 607/61 |

FOREIGN PATENT DOCUMENTS

| | | |
|---|---|---|
| WO | WO 00/24456 | 3/1998 |
| WO | WO 98/11942 | 3/1998 |
| WO | WO 00 72899 | 12/2000 |

OTHER PUBLICATIONS

USPTO Office Action for U.S. Appl. No. 10/876,058, dated Dec. 6, 2006.
USPTO Office Action for U.S. Appl. No. 10/876,058, dated Jul. 20, 2007.
USPTO Office Action for U.S. Appl. No. 10/876,313, dated Mar. 28, 2007.
USPTO Office Action for U.S. Appl. No. 10/876,313, dated Aug. 7, 2007.
Office Action, U.S. Appl. No. 10/876,058, Jan. 8, 2008, pp. 1-10.
Examination Report dated Jul. 17, 2008 for Application No. EP 05 253 919.4.
European Search Report dated Sep. 30, 2005 for Application No. EP05253917.
European Search Report dated Oct. 19, 2005 for Application No. EP05253919.
European Search Report dated Oct. 21, 2005 for Application No. EP05253920.
Examination Report dated Jul. 29, 2008 for Application No. EP05253917.
Examination Report dated Oct. 27, 2006 for Application No. EP05253920.
Examination Report dated Apr. 5, 2007 for Application No. EP05253920.
Examination Report dated Dec. 14, 2007 for Application No. EP05253920.

* cited by examiner

LOW FREQUENCY TRANSCUTANEOUS ENERGY TRANSFER TO IMPLANTED MEDICAL DEVICE

CROSS REFERENCE TO RELATED APPLICATIONS

The present application is related to four co-pending and commonly-owned applications filed on even date herewith, the disclosure of each being hereby incorporated by reference in their entirety, entitled respectively:

"TRANSCUTANEOUS ENERGY TRANSFER PRIMARY COIL WITH A HIGH ASPECT FERRITE CORE" to James Giordano, Daniel F. Dlugos, Jr. and William L. Hassler, Jr., Ser. No. 10/876,313;

"MEDICAL IMPLANT HAVING CLOSED LOOP TRANSCUTANEOUS ENERGY TRANSFER (TET) POWER TRANSFER REGULATION CIRCUITRY" to William L. Hassler, Jr., Ed Bloom, Ser. No. 10/876,038, now abandoned;

"SPATIALLY DECOUPLED TWIN SECONDARY COILS FOR OPTIMIZING TRANSCUTANEOUS ENERGY TRANSFER (TET) POWER TRANSFER CHARACTERISTICS" to Resha H. Desai, William L. Hassler, Jr., Ser. No. 10/876,057; and "LOW FREQUENCY TRANSCUTANEOUS TELEMETRY TO IMPLANTED MEDICAL DEVICE" to William L. Hassler, Jr., Ser. No. 10/876,058.

FIELD OF THE INVENTION

The present invention relates, in general, to medically implantable devices that receive transcutaneous energy transfer (TET), and more particularly, such implant devices that optimize power transfer.

BACKGROUND OF THE INVENTION

In a TET system, a power supply is electrically connected to a primary coil that is external to a physical boundary, such as the skin of the human body. A secondary coil is provided on the other side of the boundary, such as internal to the body. With a subcutaneous device, both the primary and secondary coils are generally placed proximate to the outer and inner layers of the skin. Energy is transferred from the primary coil to the secondary coil in the form of an alternating magnetic field. The secondary coil converts the transferred energy in the AC magnetic field to electrical power for the implant device, which acts as a load on the secondary coil.

In a TET system, the primary and secondary coils are placed on separate sides of the boundary or skin. This separation typically results in variations in the relative distance and spatial orientation between the coils. Variations in the spacing can cause changes in the AC magnetic field strength reaching the secondary coil, in turn causing power fluctuations and surges in the implant device. Implant devices, such as those used in medical applications, usually rely upon a microcontroller to perform various functions. These microcontrollers require a consistent, reliable power source. Variations in the supplied power, such as sudden changes in voltage or current levels, may cause the device to perform erratically or fail to function at all. Accordingly, one issue associated with conventional TET systems is that the physical displacement of either the primary or secondary coils from an optimum coupling position may cause an unacceptable effect on the output power supplied to the implanted device.

As an example of an implantable device that may benefit from use of TET is an artificial sphincter, in particular an adjustable gastric band that contains a hollow elastomeric balloon with fixed end points encircling a patient's stomach just inferior to the esophago-gastric junction. These balloons can expand and contract through the introduction of saline solution into the balloon. In generally known adjustable gastric bands, this saline solution must be injected into a subcutaneous port with a syringe needle to reach the port located below the skin surface. The port communicates hydraulically with the band via a catheter. While effective, it is desirable to avoid having to adjust the fluid volume with a syringe needle since an increased risk of infection may result, as well as inconvenience and discomfort to the patient.

To that end, in the above-referenced co-pending applications, an implanted infuser device regulates the flow of saline without requiring injection into the subcutaneous port. This system instead transfers AC magnetic flux energy from an external primary coil to a secondary coil that powers the pump in the implant connected to the gastric band within the abdomen. Although TET is not required for powering the device, the long-term nature of these devices benefits from use of TET, allowing an implanted device of reduced size and complexity. Moreover, these devices may remain unpowered between adjustments, which provides additional advantages such as not requiring a battery.

It is known to surgically implant a medical device such as, for example, a cardiac pacemaker or an adjustable gastric band, under the surface of a patient's skin to achieve a number of beneficial results. In order to actively operate within a patient, these medical implants require a reliable, consistent power source. Currently, medical implants are powered by either non-rechargeable batteries, rechargeable batteries that use a TET system to recharge the batteries, or directly by a TET system. In order to transfer sufficient power to the secondary coil of the TET system to operate an implant, TET systems have typically operated at frequencies from 100 kHz to upwards of 30 MHz. At these higher frequency levels, the alternating electromagnetic field that the primary coil generates couples not only to the secondary coil, but also to any metallic objects near it, including a metallic implant case. This parasitic coupling produces eddy currents in the implant case. These eddy currents reduce the amount of effective power transferred to the secondary coil, thereby increasing the amount of power required from the primary coil to drive the implant. In addition, the eddy currents can cause heating of the metallic case. Heating a metallic implant case by more than 2° Celsius above normal body temperature can have derogatory effects on the implant recipient. The level of eddy currents produced in a metallic object is directly proportional to the alternating magnetic field frequency raised to the second power. Accordingly, the greater the frequency of the energy transfer signal, the greater the eddy currents and energy transfer losses. In addition, operating a TET system at frequencies above 100 kHz requires that the system conform to FCC regulations.

To reduce the problems associated with eddy currents and power transfer losses when using a TET system with an implant, it has traditionally been necessary to enclose the implant in a non-metallic material, such as a ceramic outer casing, or to place the secondary coil outside of the implant outer casing and connect the coil by a pair of leads extending into the casing. Alternatively, TET systems have been used as low energy trickle charge systems that operate continuously to recharge internal implant batteries. Each of these solutions to the eddy current problem, however, is either expensive, cumbersome, or increases the complexity of the implant device. Accordingly, in order to reduce the problem of eddy currents when powering an implant, and minimize the issue of FCC regulations, it is desirable to have an energy transfer system that operates at low frequencies. In particular, it is desirable to provide a high power, low frequency TET system in which the secondary coil may be encased within the implant without significant power losses or development of eddy currents.

Although such TET powering of an implant, such as to recharge batteries, is a generally known procedure, using TET for an artificial sphincter system, such as an adjustable gastric band, presents a number of challenges. Adjustable gastric bands are most beneficial to patients that are morbidly obese. Providing a secure location to subcutaneously attach an implant that presents a reduced incident of discomfort often means that the implant is under a thick layer of skin and adipose tissue. A major challenge in using TET thus is transferring magnetic energy between the primary and secondary coils through this thick layer of dermal tissue, which thus reduces the effective amount of power transferred to the implant.

Consequently, a significant need exists for enhancing TET power transfer through the dermis of a patient and into a hermetically sealed case of an implanted medical device without significant power losses.

BRIEF SUMMARY OF THE INVENTION

The invention overcomes the above-noted and other deficiencies of the prior art by providing a transcutaneous energy transfer (TET) system that advantageously transmits between 1 to 100 kHz, thereby achieving an electromagnetic pattern that may more efficiently penetrate a physical boundary such as a metallic case of an implant or human tissue, without excessive power loss due to eddy currents, thereby avoiding heating.

In one aspect of the invention, the transcutaneous energy transfer (TET) system has an external primary power supply that energizes an external primary resonant circuit having a primary coil in electrical communication with a capacitance to form a resonant tank circuit having peak resonance within a range of 1 to 100 kHz. The TET power therefrom reaches an internal secondary resonant circuit including a secondary coil in electrical communication with a capacitance to form a resonant tank circuit having peak resonance within a range of 1 to 100 kHz to power an electrical load.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF INVENTION

Figure 1:
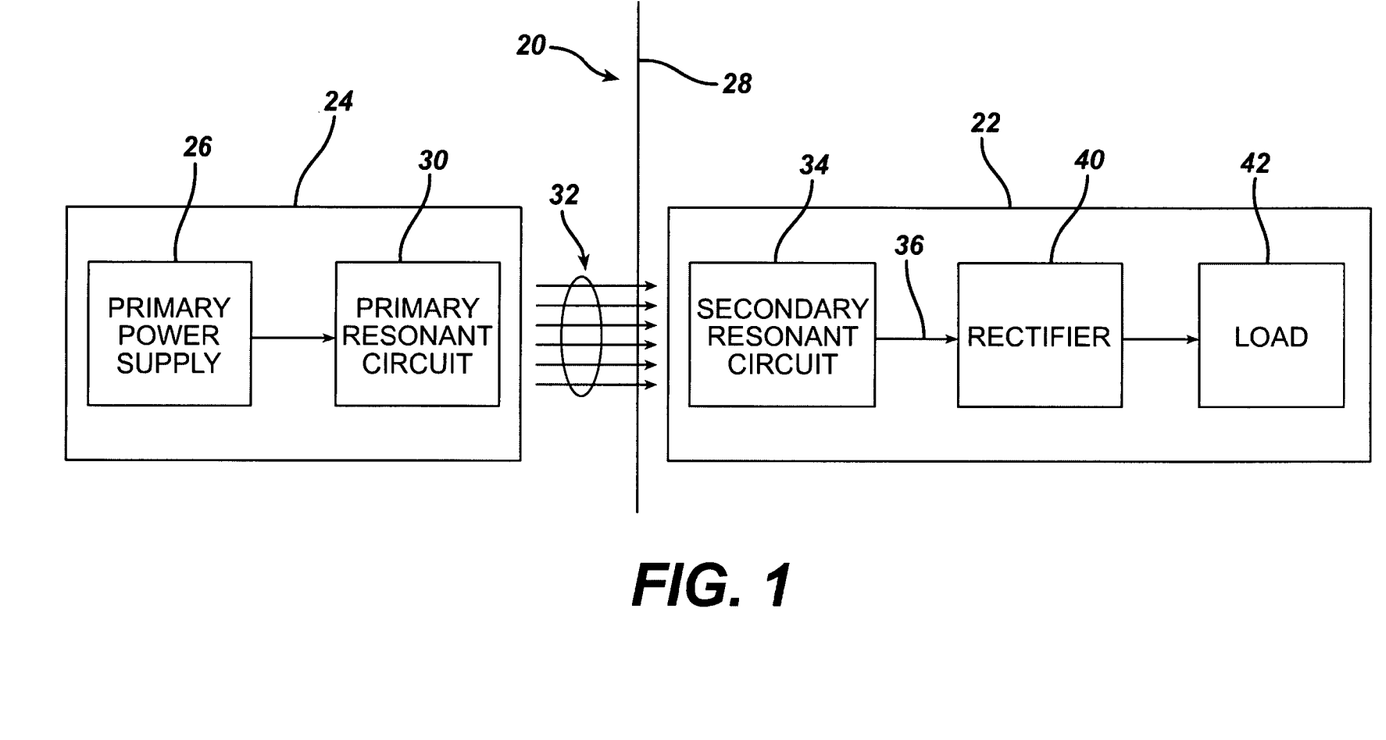
FIG. 1 is a block diagram illustrating an exemplary energy transfer system in accordance with the present invention.

Referring now to the drawings in detail, wherein like numerals indicate the same elements throughout the views, FIG. 1 depicts the relationship between a transcutaneous energy transfer (TET) system 20 for an implant device 22 in accordance with the present invention. As shown in FIG. 1, TET system 20 includes a primary circuit 24 comprising a power supply 26 located external to a physical boundary 28. Boundary 28 may be the skin of a human or animal body, such as in the case of a medical implant, or may be any other type of inanimate material or tissue depending upon the particular application of TET system 20. Primary circuit 24 also includes a primary resonant circuit 30 that is electrically coupled to power supply 26 to resonate at a designated power signal frequency. An alternating magnetic field 32 is generated in primary coil 30 in response to an electrical signal provided by power supply 26.

TET system 20 also includes a secondary resonant circuit 34 in a spaced relationship from primary resonant circuit 30. Secondary resonant circuit 34 is located on the opposite side of boundary 28 from primary resonant circuit 30 within implant 22. Secondary resonant circuit 34 is electrically coupled to primary resonant circuit 30 via alternating magnetic field 32, symbolically illustrated in the figures as arrows emanating from primary resonant circuit 30 and propagating towards secondary resonant circuit 34. Secondary resonant circuit 34 generates an electrical signal 36 from field 32. Signal 36 is rectified by a filter 40 and applied to an implant load 42 to operate the implant 22.

Implantable, bi-directional infusing devices that would benefit from enhanced TET powering and telemetry are disclosed in four co-pending and co-owned patent applications filed on May 28, 2004, the disclosure of which are hereby incorporated by reference in their entirety, entitled (1)) "PIEZO ELECTRICALLY DRIVEN BELLOWS INFUSER FOR HYDRAULICALLY CONTROLLING AN ADJUSTABLE GASTRIC BAND" to William L. Hassler, Jr., Ser. No. 10/857,762; (2) "METAL BELLOWS POSITION FEED BACK FOR HYDRAULIC CONTROL OF AN ADJUSTABLE GASTRIC BAND" to William L. Hassler, Jr., Daniel F. Dlugos, Jr., Rocco Crivelli, Ser. No. 10/856,971; (3) "THERMODYNAMICALLY DRIVEN REVERSIBLE INFUSER PUMP FOR USE AS A REMOTELY CONTROLLED GASTRIC BAND" to William L. Hassler, Jr., Daniel F. Dlugos, Jr., Ser. No. 10/857,315; and (4) "BI-DIRECTIONAL INFUSER PUMP WITH VOLUME BRAKING FOR HYDRAULICALLY CONTROLLING AN ADJUSTABLE GASTRIC BAND" to William L. Hassler, Jr., Daniel F. Dlugos, Jr., Ser. No. 10/857,763.

Figure 2:
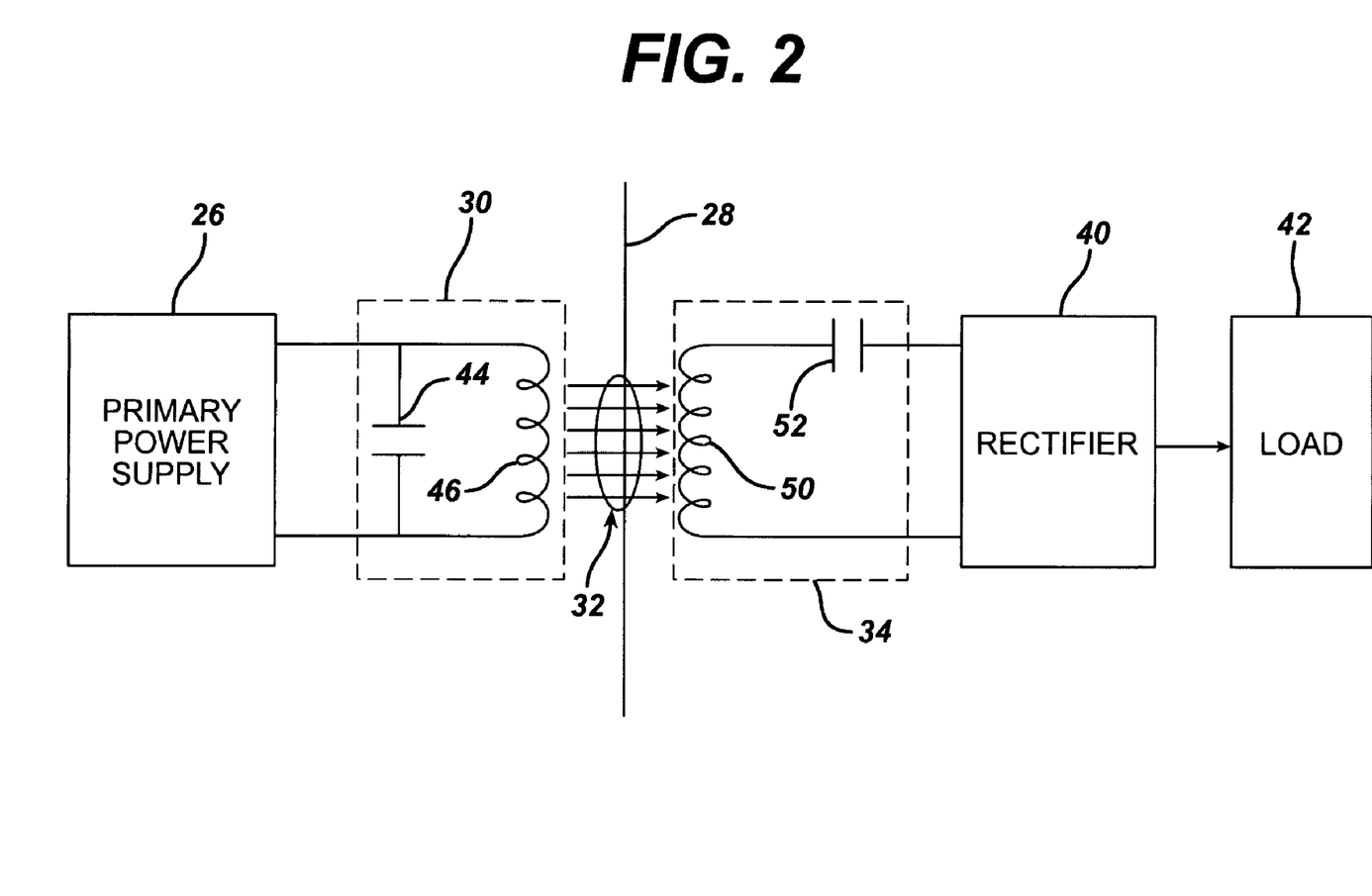
FIG. 2 is a block diagram illustrating the low frequency TET system of the present invention.

FIG. 2 provides a more detailed schematic of the energy transfer system 20 of the present invention. As shown in FIG. 2, primary resonant circuit 30 comprises a tuned tank circuit having a capacitance made up of one or more capacitors 44 connected in parallel with an inductive coil 46. Capacitance 44 and coil 46 are selected to resonate at a particular frequency when connected to power supply 26. In order to transfer power to secondary resonant circuit 34 without generating excessive eddy currents, primary resonant circuit 30 is designed to operate at low frequency levels. For purposes of this discussion, the terms "low frequency" and "low frequency level" refer to frequencies below 100 kilohertz (kHz). In order to transmit sufficient power to drive implant 22 at low frequency levels, capacitor 44 and coil 46 are selected to maximize the Q or quality factor of the circuit 30 and, thus, produce a high gain from resonant circuit 30. In the embodiment described herein, capacitor 44 and coil 46 are selected to produce a Q factor exceeding 100.

To obtain a high Q factor at a low signal frequency level, capacitor 44 is selected so as to provide a high voltage at a minimum equivalent series resistance (ESR). An example of a suitable type of capacitor for obtaining high voltage/low ESR performance is a chip-on-glass (COG) dielectric capacitor. Additionally, to maximize the Q factor of primary resonant circuit 30, coil 46 is formed so as to minimize the coil impedance and, thus, the power loss in the circuit. One method for minimizing coil impedance in the present invention is to form coil 46 from Litz wire. Litz wire is composed of individual film insulated wires that are braided together to form a single conductor. The Litz wire minimizes power losses in coil 46 due to the skin effect, or tendency of radio frequency current to be concentrated at the surface of the conductor. In addition to Litz wire, other types of high current, low power loss conductors may also be utilized for primary coil 46 in the present invention without departing from the scope of the invention. The combination of the high voltage capacitance with a high current/low power loss coil enables primary resonant circuit 30 to transfer sufficient power to drive an implant, such as, for example, 1 to 4 watts of power, by virtue of using a low transfer signal frequency.

As shown in FIG. 2, secondary resonant circuit 34 comprises a secondary coil 50 that is electrically connected in series with one or more capacitors 52 to form a series tuned tank circuit. Capacitor 52 may be any type of capacitor that enables the tank circuit to resonate in a frequency range that encompasses the resonant frequency of primary circuit 30. Similarly, coil 50 may be any type of conductor that produces minimum impedance while effectively coupling with primary resonant circuit 30 to transmit sufficient power for operating load 42. Secondary resonant circuit 34 is tuned to have a lower Q and broader bandwidth than primary resonant circuit 30 in order to couple with a broader range of resonant frequencies, and eliminate the need to individually tune the secondary resonant circuit to a particular primary resonant circuit, although it should be appreciated that a higher Q may be used.

Figure 3:
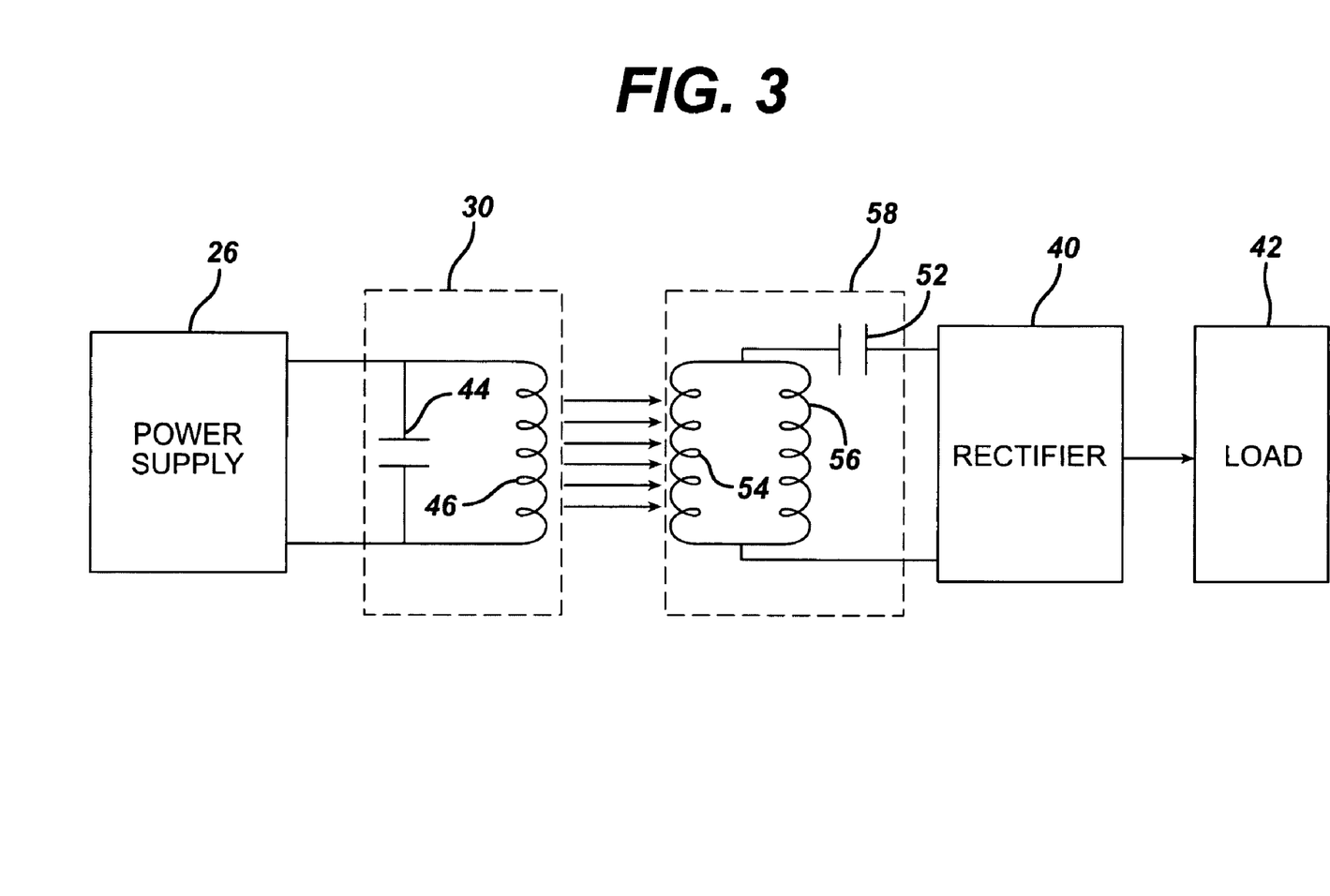
FIG. 3 is a block diagram of a second embodiment for the secondary resonant circuit.

FIG. 3 illustrates an alternative version for TET system 20 in which secondary coil 50 is replaced with a pair of inductive coils 54, 56 connected in parallel. Coils 54,56 are connected in series with capacitor 52 to form a series tuned tank circuit 58, which couples with primary resonant circuit 30 to transfer power to load 42. Replacing secondary coil 50 with parallel coils 54, 56 increases the amount of magnetic flux 32 intercepted by the secondary resonant circuit, and the amount of power supplied to load 42.

Figure 4:
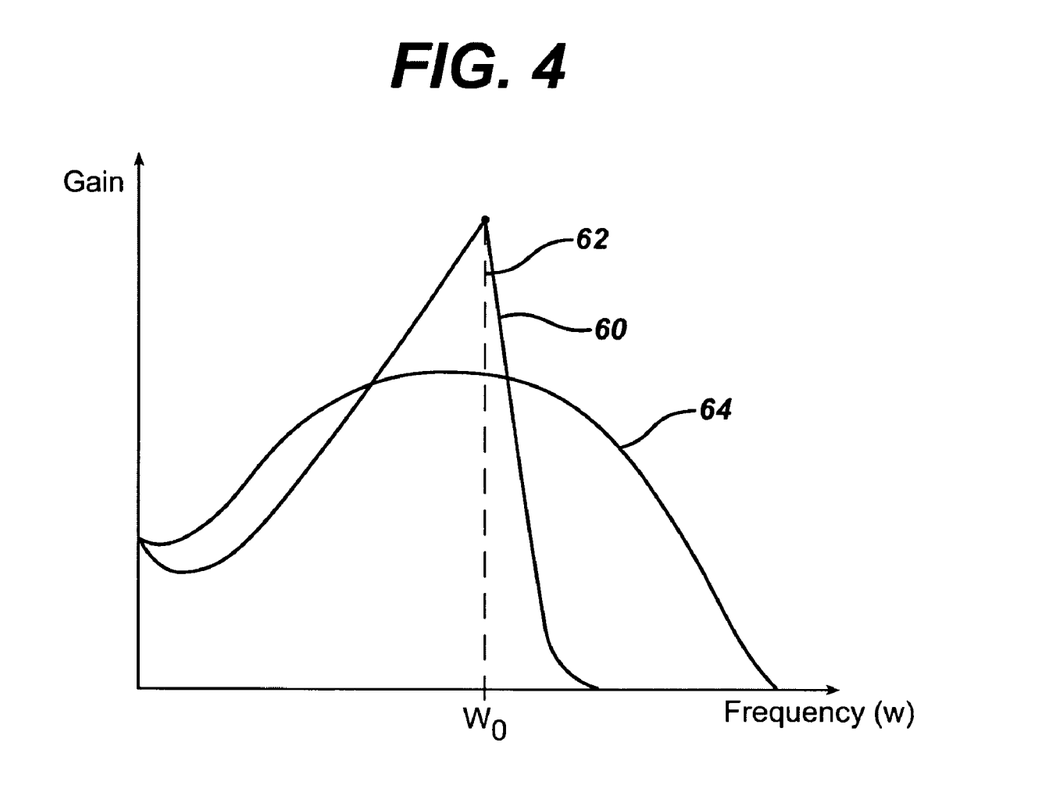
FIG. 4 is a graphical representation of the gain verses frequency response of the primary and secondary resonant circuits.

FIG. 4 provides a graphical representation of the gain verses frequency response of primary resonant circuit 30 and secondary resonant circuit 34. As shown in FIG. 4, primary resonant circuit 30 is very frequency selective, as indicated by the steep curve 60, thereby producing a high Q and power level at a narrow range of frequencies centered on the resonant frequency 62. Conversely, secondary resonant circuit 34 has a significantly lower Q than primary resonant circuit 30 and is less frequency selective as indicated by the more rounded curve 64. The broader bandwidth of secondary resonant circuit 34 desensitizes the circuit to shifts in the resonant frequency of the primary circuit 30, thus enabling the secondary resonant circuit 34 to couple with one or more different primary circuits without having to be specifically tuned to the primary circuit resonant frequency 62.

In an exemplary embodiment of the present invention, a TET system was experimentally produced having a resonant frequency range of between 1.6 and 1.7 kilohertz and a Q factor greater than 100. In this experimental circuit, primary coil 46 having an outer diameter of 5.25 inches was comprised of one hundred two (102) turns of Litz wire. The Litz wire was comprised of 100 strands of individually insulated thirty (30)-gauge magnet wire. The primary coil was placed in parallel with 9.4 microFarads of capacitance. The capacitance was a high voltage, high current, low ESR, COG dielectric capacitor. In addition, a ferrite core was incorporated with the primary coil 46 as described in the application incorporated by reference above, entitled "TRANSCUTANEOUS ENERGY TRANSFER PRIMARY COIL WITH A HIGH ASPECT FERRITE CORE"

The secondary resonant circuit was comprised of two coils connected in parallel. Each of the coils consisted of 325 turns of thirty-four (34)-gauge magnet wire. The coils each had an outer diameter of 2.4 inches. The parallel secondary coils were connected in series with a capacitance of 1.1 microFarads to create a series tuned tank circuit having a significantly lower Q than the primary resonant circuit. In the experimental circuit, the secondary circuit had a Q in the range of approximately ten (10) to fifteen (15). The experimental TET system transmitted approximately one watt of power between the primary and secondary circuits. The lower Q factor of the secondary resonant circuit enabled the circuit to couple with the primary resonant circuit without being specifically tuned and matched to the primary circuit. This exemplary circuit illustrates one configuration through which the present invention may be implemented. Additional circuit configurations and elements that maximize the Q factor of the primary resonant circuit may also be utilized to achieve low frequency TET power transfer in accordance with the present invention without departing from the scope of the invention.

Figure 5:
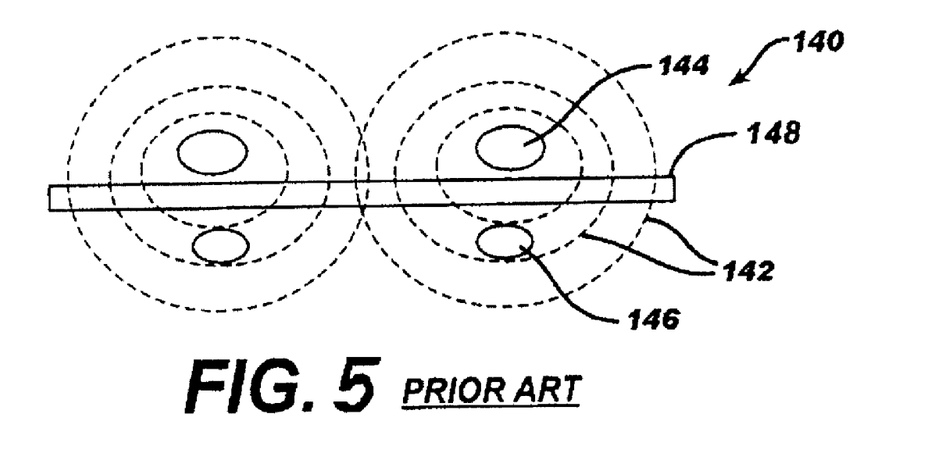
FIG. 5 is a magnetic flux diagram of a prior art TET system having a primary coil and implanted secondary coil.

FIG. 5 shows a generally known prior art TET device 140 that achieves a magnetic field, depicted as shallow flux lines 142 between parallel primary and secondary TET coils 144, 146. Primary coil 144 transfers magnetic flux 142 through an abdominal wall 48 to the secondary coil 146. Due to losses and the shape of the magnetic field 142, the secondary coil 146 is constrained to be placed relatively close to the exterior of the abdominal wall 148 since the magnetic field 142 has a circular toroidal shape that does not achieve optimal energy transfer between the two coils 144, 146.

Figure 6:
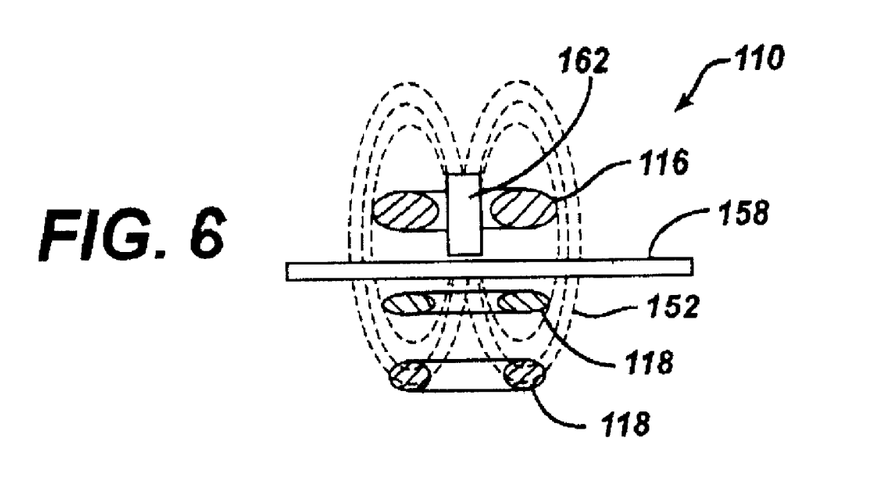
FIG. 6 is a cross section view of a magnetic flux diagram of a TET system having a magnetic flux conducting core centered within the primary coil to shape a resultant magnetic flux.

FIG. 6 depicts a TET system 110 having a ferrite core that advantageously shapes a TET magnetic field 152 into an elliptical shape that more efficiently operates through an abdominal wall 158 of a patient. Thus, at an implanted depth equivalent to the prior art secondary coil 118, more power is transferred. Alternatively, a secondary coil 118' may be placed at a greater depth for more secure attachment and enhanced patient comfort yet be able to receive sufficient power. In particular, a ferrite rod 162 aligned at a circular center of an external primary coil 116, shaping the magnetic flux 152 formed an elliptical toroidal shape, causing an increase in flux density within the secondary coil 18.

Figure 7:
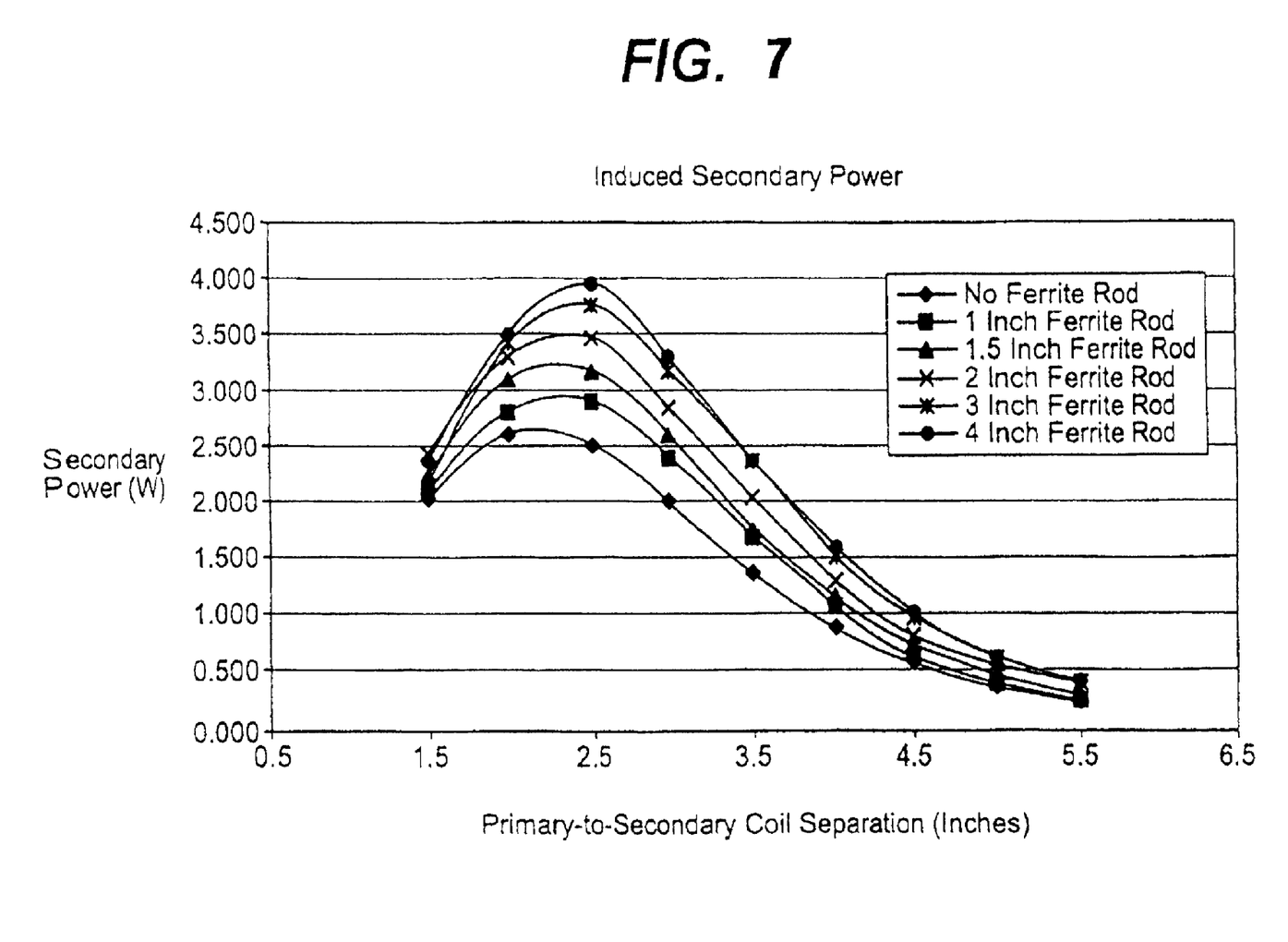
FIG. 7 is a plot of power induced in a secondary coil by various lengths of a flux shaping core in the primary coil and different depths of separation between primary and secondary coils.

This enhanced power transfer is depicted in FIG. 7, showing the difference in energy transfer efficiency before and after placement of the ferrite cores 62 of different lengths into the primary coil 16. It was shown that a benefit existed for additional power received in the secondary circuit for separation distances of 1.5 to 5.5 inches by the inclusion of a core of lengths between 1 to 4 inches. Extrapolating from the results indicates that some benefit would be appreciated by a shorter length of a core, if constrained by available clearance considerations. In addition, longer lengths of a core may be used to obtain additional power coupling efficiencies.

To achieve the greatest energy transfer efficiency, a highly magnetically permeable ferrite core 162 has been placed within the primary coil 116. The optimum core 162 is of a long, skinny design. Testing indicates that a ferrite core rod 162 with a length of about 3 inches and a width of about 0.75 inches is the optimal size for the given primary coil 116 at which energy transfer is at its most efficient without going into magnetic saturation or wasting energy in the form of eddy current losses within the core 162.

With the long and slender core design, most of the magnetic flux is drawn toward the ferrite core 162, causing the field to collapse radially into the core 162 and changing the shape of the field 152 from circular to elliptical. This effect leads to an increase in the flux density within the secondary coil 18. In an exemplary version, a ferrite core of 3 inches length and 0.75 inches diameter was placed within the center of a 5 inch diameter primary coil 116 of the transcutaneous energy transfer (TET) system 10. With the addition of this core 162, the power coupling efficiency to the secondary TET coil was increased by up to 55%.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

What is claimed is:

1. A transcutaneous energy transfer (TET) system for communicating energy from the exterior of a patient to an internal implant, comprising:
   a) an external primary power supply;
   b) an external primary resonant circuit energized by the primary power supply and including an annular primary coil in electrical communication with capacitance to form a resonant tank circuit having peak resonance at or below 100 kHz, the annular primary coil further comprising:
      i) at least one wire wrapped repeatedly about a primary center axis of the primary transmitter coil into a toroid having an annular cross section, wherein the toroid encircles the primary center axis to form an annular ring shape,
      ii) a primary circular gap about the primary center axis, the primary circular gap defined by and encircled by the annular ring shape of the primary transmitter coil, and
      iii) an elongate ferrite core extending through the gap of the annular ring shape and the center point, the elongate ferrite core being oriented substantially perpendicular to the annular ring shape and extending in a straight line above and below the center point to define a longitudinal axis, the elongate ferrite core only having a first end above the annular ring shape and a second end below the annular ring shape with a uniform core diameter extending therebetween from end to end, wherein the uniform core diameter is smaller than an inner diameter of the circular gap,
   c) an internal electrical load comprising a device implantable within the patient; and
   d) an internal secondary resonant circuit implantable within the patient and including an annular secondary coil in electrical communication with the annular primary coil to form a resonant tank circuit having peak resonance at or below 100 kHz and to receive TET power from the annular primary coil for powering the internal electrical load, the annular secondary coil further comprising:
      i) at least one wire wrapped about a secondary center axis of the annular secondary coil into a toroid having an annular cross section, wherein the annular secondary coil encircles the secondary center axis of the annular secondary coil to define a second annular ring shape with an exterior secondary diameter, and
      ii) a secondary circular gap between the secondary center axis and the annular secondary coil;
   wherein when the annular secondary coil is implanted within the patient with the exterior secondary diameter substantially parallel to and spaced internally away from the skin, the annular primary coil and the elongate ferrite core are oriented above the skin of the patient with the longitudinal axis of the elongate ferrite core oriented substantially coaxially with the primary center axis of the annular primary coil and with the secondary center axis of the implanted annular secondary coil, and with the annular primary coil and the annular secondary coil substantially perpendicularly aligned with the longitudinal axis, and
   the annular primary coil is energized to communicate directly with the implanted annular secondary annular coil via an elliptical toroidal electromagnetic energy field, wherein the elongate ferrite core elongates the elliptical toroidal electromagnetic energy field above and below the annular primary coil and along the longitudinal axis to transfer energy directly to the annular secondary coil and the energy transfer is optimized by the elongation of the toroidal electromagnetic energy field to maximize the power transmission and to maximize implant depth for operative transfer of energy from the external annular primary coil to the annular secondary coil when the annular secondary coil is implanted in a patient.

2. The TET system of claim 1, wherein the internal secondary resonant circuit further comprises a pair of annular secondary coils physically and electrical in parallel.

3. The TET system of claim 1, wherein the wire of the annular primary coil comprises multi-turn insulated Litz wire.

4. The TET system of claim 1, wherein the capacitance comprises a chip-on-glass dielectric capacitor.

5. The TET system of claim 1, wherein the wire of the annular secondary coil comprises Litz wire.

6. The TET system of claim 1, further comprising rectification filtering between the secondary resonant circuit and the electrical load.

* * * * *